United States Patent [19]
Miller

[11] Patent Number: 5,301,168
[45] Date of Patent: Apr. 5, 1994

[54] ULTRASONIC TRANSDUCER SYSTEM

[75] Inventor: David G. Miller, Boxford, Mass.

[73] Assignee: Hewlett-Packard Company, Palo Alto, Calif.

[21] Appl. No.: 6,084

[22] Filed: Jan. 19, 1993

[51] Int. Cl.⁵ .............................. G03B 42/06
[52] U.S. Cl. ..................... 367/138; 367/11; 367/105; 128/661.01
[58] Field of Search .............. 367/7, 11, 138, 103, 367/105; 128/661.01; 73/609, 610

[56] References Cited

U.S. PATENT DOCUMENTS

| | | | |
|---|---|---|---|
| 4,140,022 | 2/1979 | Maslak | 367/105 |
| 4,359,767 | 11/1982 | Sachs et al. | 367/105 |
| 4,670,683 | 6/1987 | 't Hoen | 310/334 |
| 5,105,814 | 4/1992 | Drukarey et al. | 128/661.01 |

OTHER PUBLICATIONS

David E. Schmieder et al "A Segmented Aperture Approach to High Resolution NMMW Imaging", two pages, Georgia Institute of Technology, Engineering Experiment Station, Atlanta, Ga 30332.

Primary Examiner—Daniel T. Pihulic

[57] ABSTRACT

An ultrasonic transducer is provided which has multiple apertures in at least the elevation direction, and preferably in both the elevation and azimuth direction. Each aperture has a selected focal length, with the focal length increasing with the size of the aperture. By transmitting multiple scan lines at a given angle using the different apertures and line splicing received echo signals, resolution is enhanced by utilizing only the portion of each received scan line for which the corresponding elevation aperture is focused. While different controlled elevation apertures may be utilized for transmit and receive, the same aperture is preferably used for both. Additional techniques are discussed for both further enhancing resolution and for mitigating the decrease in frame rate which results from shooting multiple scan lines at a given angle.

24 Claims, 16 Drawing Sheets

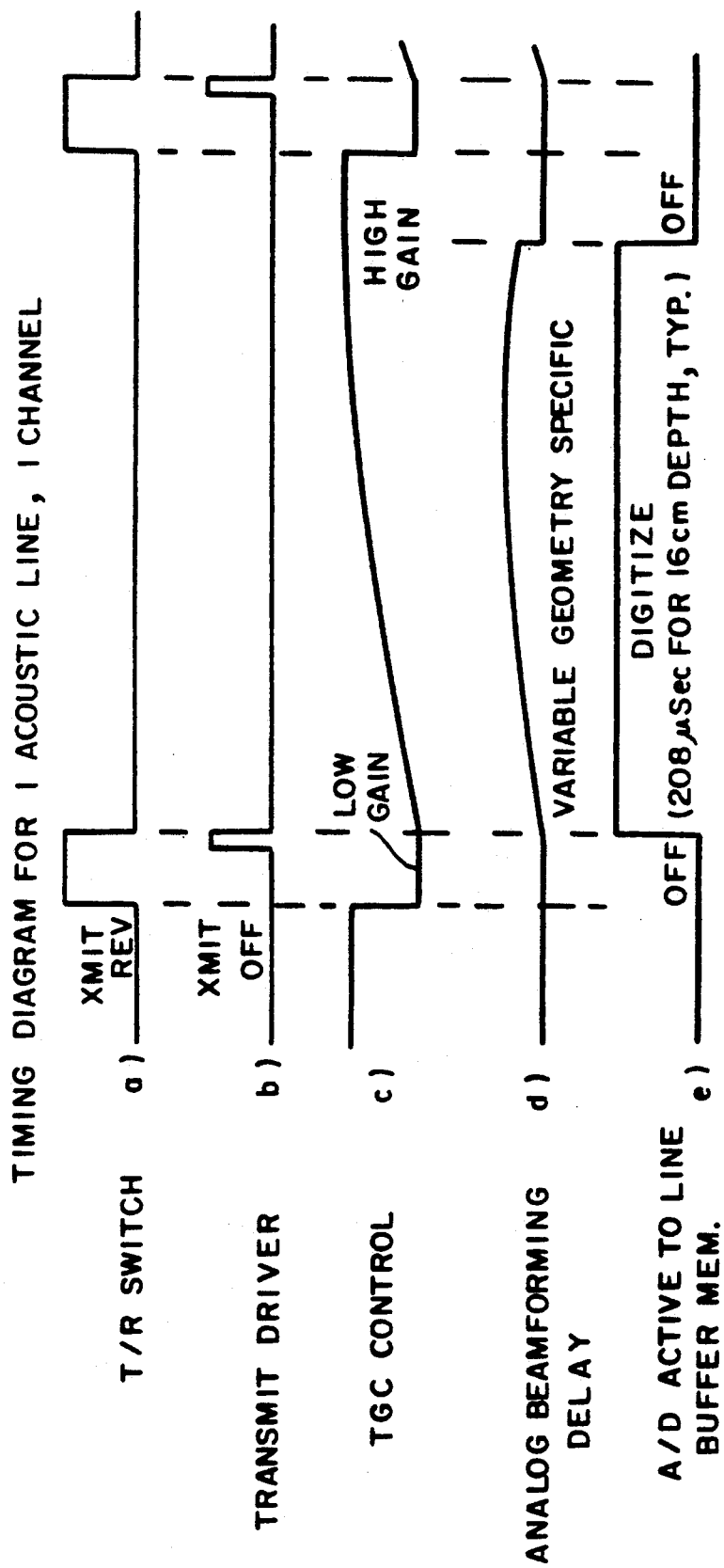

ULTRASONIC TRANSDUCER SYSTEM

FIELD OF THE INVENTION

This invention relates to ultrasonic transducer systems and, more particularly, to ultrasonic transducer systems providing enhanced focusing and thus enhanced resolution, over an extended depth range.

BACKGROUND OF THE INVENTION

Ultrasonic scanning systems are currently utilized in a variety of medical and industrial applications to non-invasively and non-destructively obtain images of organs and other body parts and of mechanical structures at depths which are not visible from the surface.

One problem with most existing ultrasonic scanning systems is that the transducer is typically focused to a predetermined depth, both for transmit and receive. This means that the ultrasonic beam is relatively wide both in the azimuth direction (which is parallel to the direction in which the transducer is typically scanned) and in the elevation direction (which is at right angles to the direction of scan) at points which are less deep than the focal point and, in particular, at points at greater depths than the focal point. Where the area of interest is only at a single depth, this may not be a problem. However, the area of interest with an ultrasonic scan typically extends over a substantial depth range. Therefore, the beam is typically focused somewhere near the midpoint of this range and is thus out of focus by varying degrees through much of the scan.

Various techniques have been utilized in the past for overcoming this problem. However, most of these techniques have continued to utilize a single transmit aperture having a single focal point for transmission and have varied aperture, generally in the azimuth direction, on receive in an attempt to maintain a more uniform f number and to obtain a variable focus. U.S. Pat. No. 4,359,767 and 4,670,683 teach the use of similar techniques to control receive focus in the elevation direction.

However, these techniques address only half of the problem in that, even though resolution may be enhanced by providing a variable receive focus as echoes from greater depths are being received, resolution is still degraded by the fact that the transmit beam is out of focus through much of the depth range of the scan. While a commercial system was recently introduced which provided multiple transmit apertures at a given steering angle in the azimuth direction, with line splicing to permit utilization of data for the appropriate transmit scan line at different depths, systems which provide the proper aperture and focus either for transmit receive in the elevation direction or for transmit and receive in both the elevation and azimuth directions do not exist in the prior art. Further, since transmitting multiple scan lines at a given steering angle results in significant reductions in frame rate, which may be unacceptable when scanning moving organs such as the heart, the prior art has not dealt with the problems of enhancing frame rate to compensate for the use of multiple transmit apertures. The availability of multiple scan lines at a particular steering angle also presents opportunities for further resolution enhancement which have not been addressed in the prior art.

A need therefore exists for an enhanced ultrasonic scanning system which provides for multiple scanning apertures in the elevation direction and/or in both the elevation and azimuth direction to provide proper transmit and receive focus at varying scan depths and thus enhanced image resolution. When doing this, it is also desirable to provide means for reducing the degradation in frame rate caused by multiple scanning apertures and to utilize the multiple scan lines being transmitted from multiple apertures at a given steering angle to obtain still greater resolution enhancement.

SUMMARY OF THE INVENTION

In accordance with the above, this invention provides an ultrasonic transducer system having an ultrasonic transducer array with N transducer elements or channels in the azimuth direction. At least selected ones of the transducer elements are divided into N segments in the elevation direction, the segments being grouped to form E elevation apertures. A transmit focus is provided for each of the elevation apertures at a selected depth, the focus depth increasing with the size of the elevation aperture. Selected transducer channel segments are energized to transmit scan lines at selected steering angles. For at least selected steering angles, the segments for at least two different elevation apertures are energized at different times, causing at least two scan lines to be transmitted at such steering angles. Echo signals are received from the transducer array in response to each energization of the transducers. The received echo signals are line spliced for the selected steering angles so as to use from each received scan line the portion thereof for which the corresponding elevation aperture is focused. In addition to controlling the elevation aperture utilized for transmitting scan lines at a given steering angle, the elevation aperture utilized for receiving each scan line may also be controlled. The receive elevation aperture utilized for a scan line is related to the transmit elevation aperture in a predetermined way to achieve a predetermined response. For a preferred embodiment, the transmit and receive elevation apertures for a given scan line are the same. For preferred embodiments, transmit focus is provided by a segmented lens having a different segment configuration for each elevation aperture to provide the desired focal depth, by a segmented transducer surface having different segment configuration for each elevation aperture or by a combination thereof.

The channels may also be grouped to form a plurality of apertures in the azimuth direction with an azimuth focus being established for each of the azimuth apertures. For a preferred embodiment, there are E azimuth apertures with the azimuth focus for each azimuth aperture being the same as the elevation focus for the corresponding elevation aperture. For these embodiments, the transducer channels and segments for at least two different ones of the apertures are energized at different times for the selected steering angles. For preferred embodiments, the segments of each elevation aperture are included in each larger elevation aperture and the selected steering angles at which at least two elevation apertures are transmitted are all steering angles at which scan lines are transmitted.

While the techniques described above wherein focused segments of scan lines are line spliced to produce the display at a given steering angle results in enhanced resolution, resolution may be still further enhanced by providing, as discussed above, a different azimuth aperture for each elevation aperture, which azimuth aperture is matched to the corresponding elevation aperture.

Similarly, resolution is enhanced by utilizing higher frequency ultrasonic signals. However, such signals are attenuated at the greater depths. Therefore, system resolution is enhanced by utilizing a frequency for each elevation aperture which is matched to the aperture depth. Line splicing may be accomplished by providing at least one line buffer with a portion of each scan line for a given steering angle which is for the depth at which the corresponding elevation aperture is focused being stored in the buffer, the desired line spliced scan line data thus being stored in the buffer after scanning at the steering angle has been completed.

In some instances, resolution may also be enhanced by transmitting scan lines for each of the E elevation apertures at a plurality of substantially uniformly spaced steering angles and transmitting scan lines for a selected number of elevation apertures less than E for steering angles intermediate the plurality of steering angles. Preferably, the selected number of elevation apertures for the intermediate steering angles are the one or more elevation apertures focused at the deeper depths where resolution is otherwise reduced by the wider spacing of the angled scan lines. The selected apertures utilized for the intermediate steering angles may also include azimuth apertures.

One disadvantage of the line splicing technique described above is that it results in a decrease in the frame rate of the system. Various techniques may be utilized to mitigate this problem by enhancing system frame rate. One such technique is to reduce the scan depth for selected scan lines. The selected scan lines having their depth reduced may be scan lines at selected steering angles, for example, the steering angles at the ends of the scan. For one embodiment, the reduction in scan depth increases as the steering angle approaches the two ends of the scan. Alternatively, the selected scan lines having their depth reduced may be the scan lines for the elevation apertures provided with the shortest focal depth, the scan depth for such scan lines corresponding to the greatest depth for which received echo signals for such scan lines are utilized for line splicing. When this technique is utilized, the scan lines may be ordered for the steering angles such that a reduced depth scan line is not followed by a long scan line at the same or near adjacent steering angle. This avoids echoes from the short scan line interfering with the subsequently generated long scan line, but may not be practical because of temporal discordance or discontinuities in the image. When this is done, a plurality of scan buffers may be required for line splicing, the portion of the scan line received at a given steering angle being assembled in a given buffer until all scan lines for the steering angle have been transmitted. The number of buffers required would generally be equal to the number of apertures E, or as a minimum to the maximum number of such apertures which may be utilized to transmit scan lines at a given steering angle.

Scan depth may be reduced by reducing the power provided to energize transducer segments for transmission. When this is done, it is generally also desired to increase the receive gain for the echo signals to maintain a desired signal level. It may also be desirable to increase the frequency for the scan line having its depth reduced since high frequency signals are attenuated more quickly than lower frequency signals.

Frame rate may also be enhanced by reducing the number of steering angles in the azimuth direction at which scan lines are transmitted. For one embodiment, the spacing between adjacent selected steering angles varies inversely with the cosine of the steering angle, permitting a reduction in the number of steering angles particularly at the ends of the scan.

For at least one embodiment, wiring into the transducer cable is reduced by providing switches at the transducer array which are operative in response to a change in the aperture being utilized for causing transducer channel segments for the appropriate aperture to be energized.

The foregoing and other objects, features and advantages of the invention will be apparent from the following more particular description of preferred embodiments of the invention as illustrated in the accompanying drawings.

IN THE DRAWINGS

FIGS. 7A and 7B are timing diagrams for one scan line and one display frame, respectively, for a conventional scan with the embodiment of the invention shown in FIG. 4.

DETAILED DESCRIPTION

Figure 1:
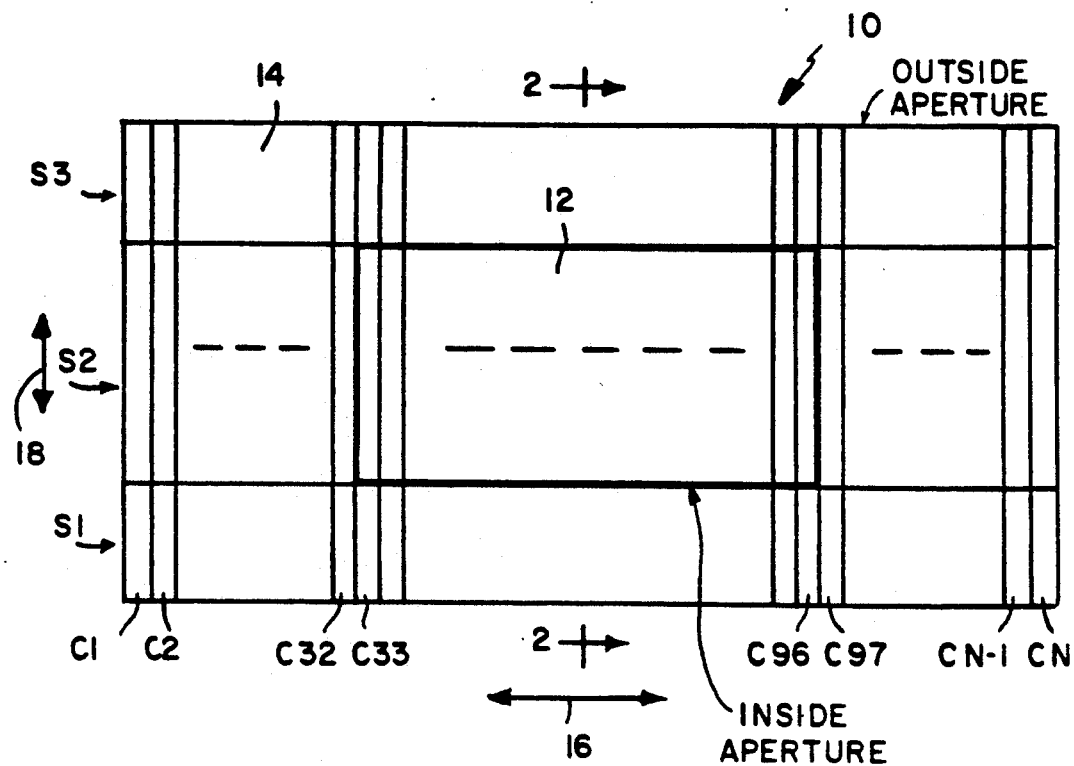
FIG. 1 is a front plane view of a two-aperture transducer array.

In FIG. 1, an ultrasonic transducer 10 is shown having an inside aperture 12 and an outside aperture 14. In the azimuth direction 16, transducer array 10 is comprised of a plurality of elements or channels C1-CN. An ultrasonic scanning transducer utilized, for example, for medical applications might have 64, 128 or 256 elements. For a preferred embodiment, the number of elements in large aperture 14 is 1.4 to 2 times that for small aperture 12. Thus, assuming a ratio of 2 and a 128 element transducer (i.e. N=128), elements C1-C32 and C97-C128 would be part of only the large aperture. Further, each aperture may be divided into a plurality of segments in the elevation direction 18. For a two-aperture transducer, each element is divided into three segments S1-S3. For a preferred embodiment, S2 is equal to the sum of S1 and S3 or, in other words, the size of inside aperture 12 in the elevation direction is half of that for outside aperture 14. As with the azimuth direction, the preferred ratio of aperture sizes in the elevation direction is 1.4 to 2. The dividing of the transducer into elements and segments may be accomplished by providing properly segmented electrodes for a unitary block of transducer material or the elements and segments may be formed by scoring or otherwise forming individual transducer elements and/or segments utilizing procedures known in the art. Thus, from FIG. 1, it is seen that inside aperture 12 is formed by the S2 segments for transducers C33-C96 while outside aperture 14 is formed by all three segments of all N transducer elements or channels. Further, it should be noted that, while for operational reasons there is no reason to segment the transducer elements of channels C1-C32 and C97-C128, and the invention could be practiced without segmenting these channels, it is normally simpler to fabricate the transducer array with all channels being segmented rather than just those utilized for inner aperture 12.

Transducer 10 is typically focused in the azimuth direction at a particular depth and steering angle by utilizing a selected aperture of the available channels and by selectively delaying the energizing of the channels and of the echo signals received over the channels. However, f number, which determines the width of the focal point, is directly proportional to range or target depth and is inversely proportional to aperture size. Thus, to obtain a substantially uniform f number, and thus a substantially uniform beam width over a range of interest, it is desirable that the aperture size increase for increasing depth both in the azimuth and elevation directions. Further, it is desirable that this variable aperture size with depth exist in both the azimuth and elevation directions to obtain true uniform beam width.

However, since only a single scan line is typically transmitted at each steering angle, heretofore aperture correction has been implemented primarily on receive, and primarily only in the azimuth direction. As will be discussed in greater detail hereinafter, this invention contemplates (a) providing variable aperture for both transmit and receive; and (b) providing such transmit and receive variable aperture in the elevation direction (and preferably in both the azimuth and elevation directions), so as to provide near optimum beam width and focus throughout at least the scan depth range of interest.

While focusing in the elevation direction can be accomplished by varying delays for the various segments, the electronics for focusing in the elevation direction in this manner, particularly when variable focusing is occurring both on transmit and receive, become fairly complex. Therefore, for a preferred embodiment of the invention illustrated in FIG. 2, lenses are provided to perform the focusing function in the elevation direction with transducer segments S1, S2 and S3 for a given channel C being simultaneously energized for transmit when large aperture 14 is being utilized. The lens 22 utilized for focusing in the elevation direction has a concave lens portion 24 which overlies the S2 transducer segments and a convex lens section 26 which overlies the entire transducer array. Lens section 24 need extend only over inner aperture 12, but preferably extends over all of the S2 segments. Lenses 24 and 26 combine to form a short focal length compound lens for inner aperture 12 with lens 26 forming a long focus lens for large aperture 14. The desired dual focus for the apertures is thus attained in the elevation direction.

Figure 2:
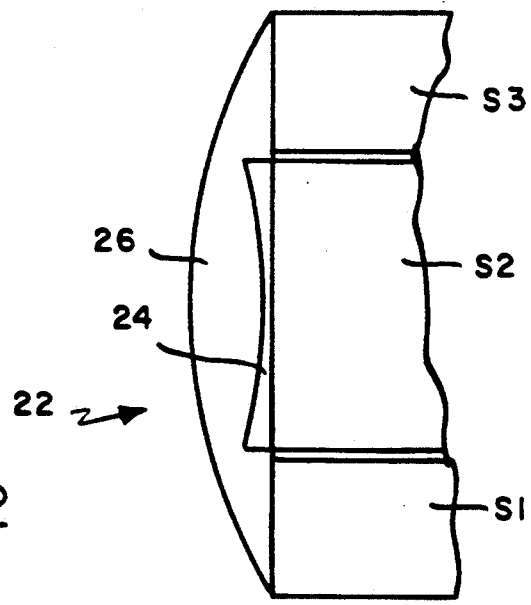
FIG. 2 is a side section view along the line 2—2 of the two-aperture transducer array shown in FIG. 1.
Figure 3A:
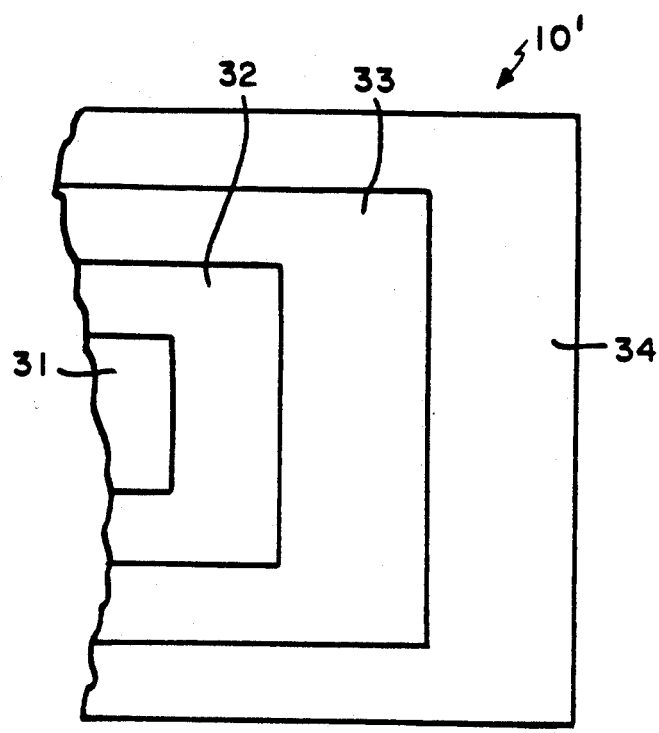
FIGS. 3A and 3B are a partial front plan view and a side sectional view, respectively, of a four-aperture transducer array.
Figure 3B:
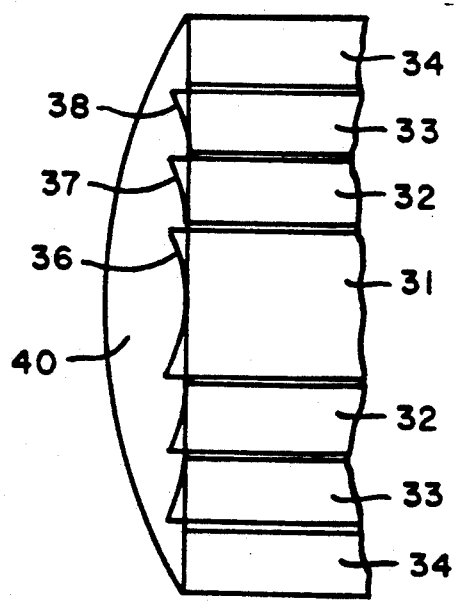

FIGS. 3A and 3B illustrate a transducer array 10' having four apertures 31-34, each aperture being in both the azimuth and elevation direction. For ease of illustration, the various channels and segments are not shown in these figures. Apertures 31, 32 and 33 are each overlaid with a concave lens section 36-38, respectively, with a convex lens section 40 overlying the entire transducer. As for the embodiment shown in FIG. 2, lenses 36, 37 and 38 may extend for the entire length of the transducer array in the azimuth direction. Lens section 36 combines with lens 40 to form a compound lens having the shortest focal length. Lens sections 37 and 38 combine with lens 40 to form compound lenses having progressively greater focal lengths, with lens 40 alone having the greatest focal length.

It should at this point be noted that while concave lenses 24, 36, 37 and 38 have been shown in FIGS. 2 and 3 for forming compound lenses to focus an aperture in the elevation direction at a desired depth, the face of the transducer array itself could be formed in the configuration of these lenses, permitting the elimination of the lenses. However, it is generally simpler to fabricate lenses than to form the face of the transducer in a desired shape. Further, in some applications, it may be desirable to use suitably shaped, simple lenses rather than compound lenses to achieve the desired focal lengths. However, such simple lenses are not preferred since they result in a jagged rather than a smooth surface for the array. Air bubbles, dirt or the like may collect in the ridges of such a surface causing opaque zones, scatter or other potential problems. Other means known in the art may also be utilized to achieve desired focal lengths.

Figure 4:
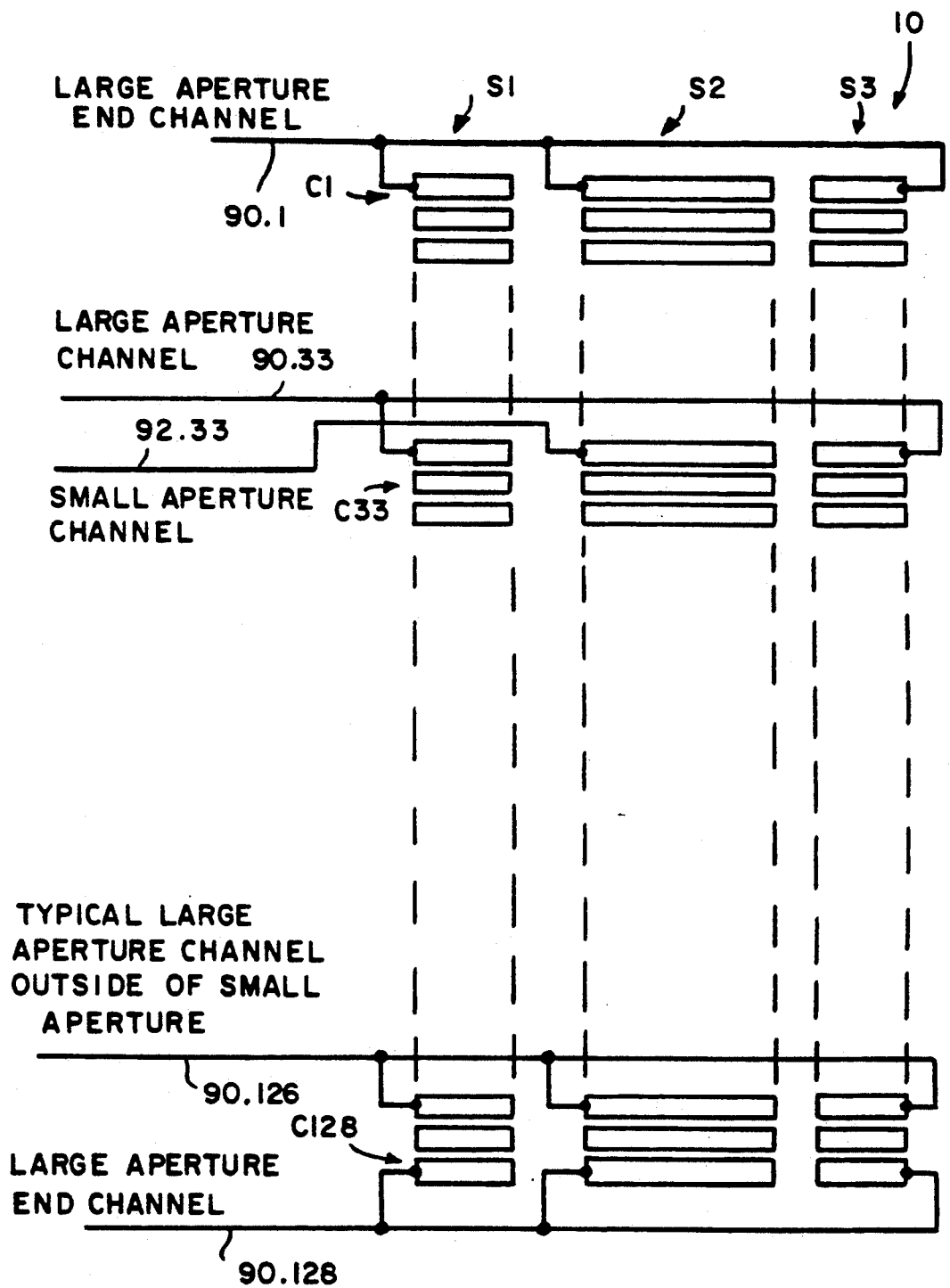
FIG. 4 is a diagram illustrating electrical connections to the transducer array segments for a two-aperture embodiment of the invention.

FIG. 4 is a diagram illustrating electrical connections to the segments of a transducer array 10. For purposes of illustration, it is again assumed that the array has 128 channels. Since each of the channels C1-C32 and C97-C128 is utilized only in the large aperture, a single large aperture line 90.1-90.128 may be connected to energize the transducer segments of each of these channels. However, for the channels C33-C96 which are utilized in both the large and small aperture, the large aperture line 90 for such channels is connected only to the two outer segments S1 and S3. A separate small aperture line 92 is utilized for each of these channels which is connected only to the center segment S2 thereof. Thus, for a preferred embodiment of the invention, only lines 92 are energized for scan lines produced by small aperture 12 (FIG. 1), while both lines 90 and line 92 are energized for the transmission and receipt of scan lines for large aperture 14. For an alternative embodiment of the invention, only lines 92 are energized for a small aperture scan and only lines 90 are energized for a large aperture scan. However, this alternative embodiment has a number of drawbacks and is not preferred.

One problem with the embodiment shown in FIG. 4 is that it requires two wires to be brought into the transducer array for each of the channels C33-C96 which can be utilized for more than one aperture. Where an array such as that shown in FIGS. 3A and 3B is utilized having four apertures, this means that as many as four separate lines must be brought in for some channels. This results in the cable connecting the head containing the transducer array being large, heavy, and very stiff, and therefore makes the system more cumbersome to utilize.

Figure 5:
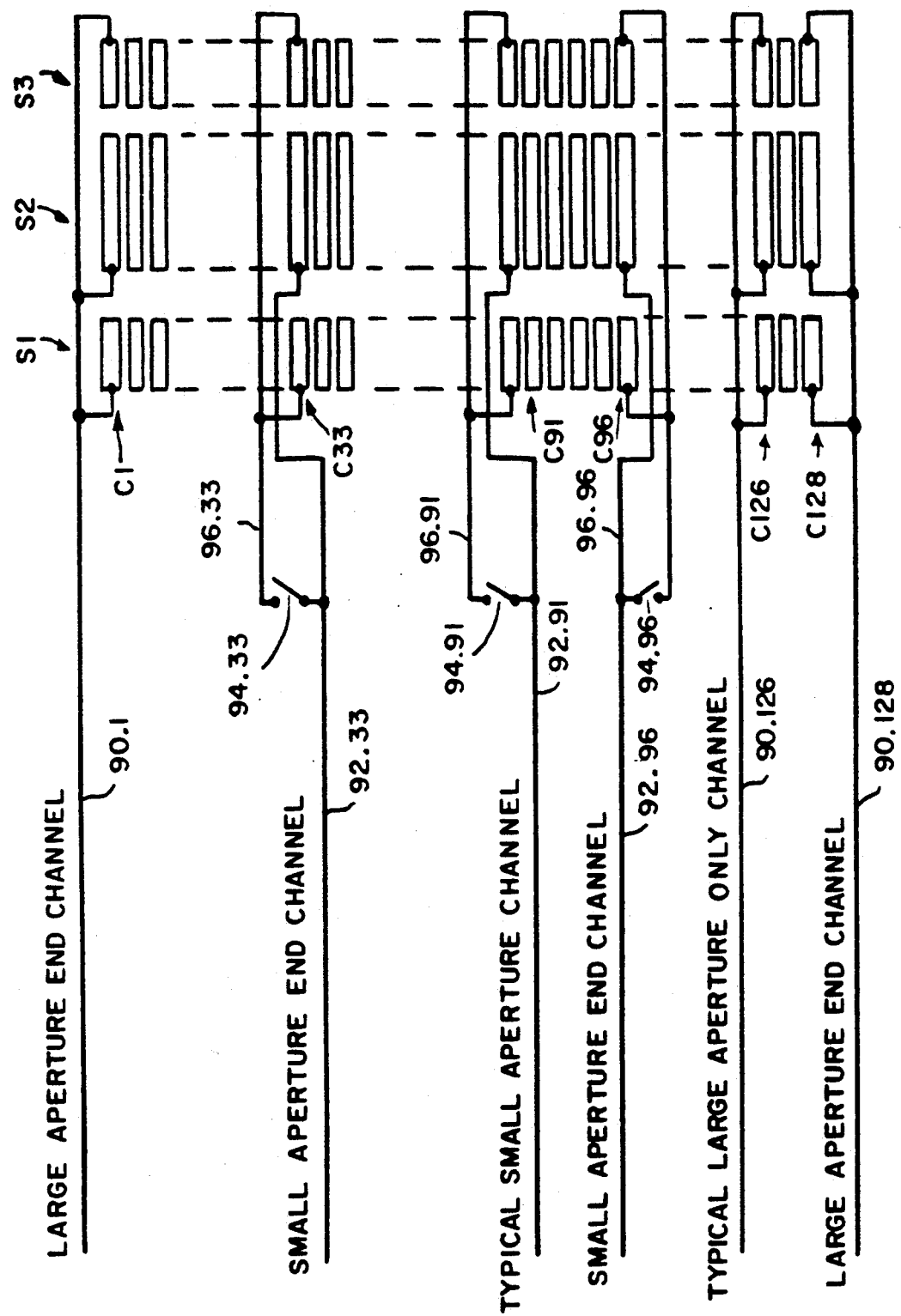
FIG. 5 is a diagram illustrating an alternative embodiment for making electrical connections to the transducer array segments of a two aperture transducer array.

FIG. 5 shows a way in which the number of lines needed to connect to a head having a multiple aperture transducer array may be reduced. Referring to FIG. 5, a single wire 90 is still connected to each of the outer channels C1-C32 and C97-C128. The lead 92 is also connected to the S2 segment for each of the channels C33-C96 utilized for the small aperture. However, instead of having a separate lead 90 for the S1 and S3 segments of each of these channels, the lead 92.33-92.96 for each of these channels is connected through a corresponding switch 94.33-94.96 to a wire 96.33-96.96 leading to the outer segments S1-S3 of the channel. The switches 94 are preferably electronic switches, for example, MOSFET's, all of which may be energized from a single lead. Thus, when a small aperture scan is to be performed, the switches 94 are deenergized or open as shown in FIG. 5 and the signals applied to line 92 thus energize only center segments S2 of the corresponding channel. When a large aperture scan is to be performed, a signal is applied to the single extra line energizing all of the switches 94 to their closed condition, resulting in the signals on lines 90 and 92 energizing all of the channel segments. The technique shown in FIG. 5 may be extended by providing an additional switch for each aperture for which a channel may be utilized and providing one extra line into the transducer head for each aperture to control energization of the corresponding switches.

Figure 6:
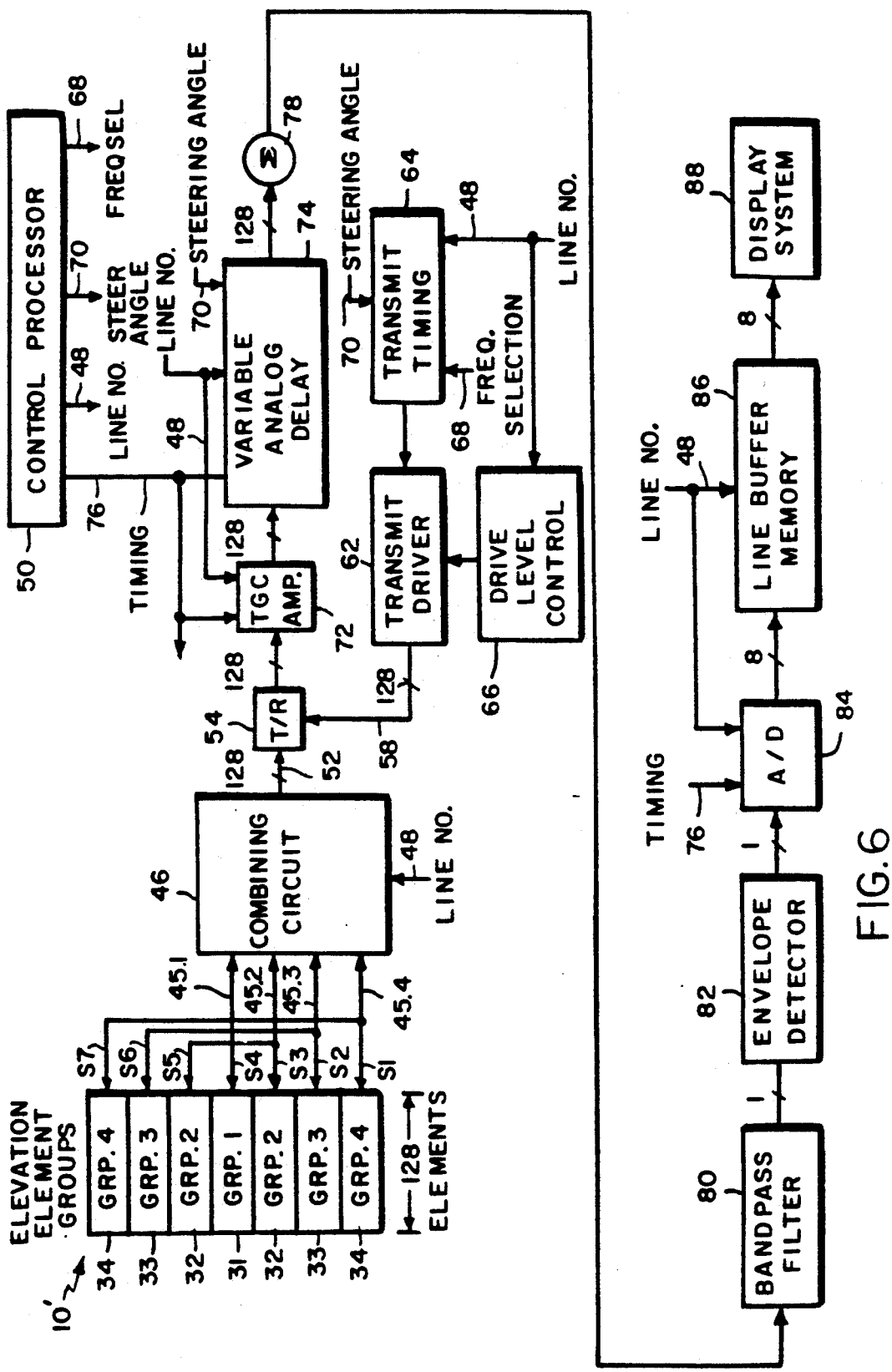
FIG. 6 is a schematic block diagram of an ultrasonic transducer system which may be utilized in practicing the teachings of this invention.

FIG. 6 is a schematic block diagram of a simplified circuit for controlling a four-aperture transducer system. While FIG. 6 is primarily concerned with controls in the elevation direction, for preferred embodiments, controls would also be provided in the azimuth direction to provide multiple apertures Referring to FIG. 6, the four-aperture transducer array has the apertures 31-34 at least in the elevation direction. The group 4 segments of aperture 34 are segments S1 and S7, the group 3 segments of aperture 33 are segments S2 and S6, the group 2 segments of aperture 32 are segments S3 and S5 and the group 1 segments of aperture 31 are segments S4. The segments of each aperture are connected through a common line 45.1-45.4 to combining circuit 46. Each of the lines 45 leading into circuit 46 is actually formed of 128 separate lines, one for each channel. An additional input to combining circuit 46 is a signal on "line number" line 48 from a control processor 50. Depending on the number of apertures and the manner of their combination, there may be a plurality of lines 48 which indicate the aperture in the elevation and/or azimuth direction currently being utilized for transmit and/or receive. Combining circuit 46 contains a plurality of switches which are preferably electronic switches such as MOSFET's, which are selectively energized in response to the input on line(s) 48 to connect appropriate transducer segments in the elevation and/or azimuth direction to line 52. Combining circuit 46 may be a hard wire circuit or may include a special purpose or suitably programmed general purpose processor for performing the switch control function. For example, circuit 46 may contain a RAM or a ROM which is addressable by lines 48 and has outputs which are selectively energized in response to an address input to control the various aperture switches.

Lines 52 connect to transmit/receive (T/R) circuit 54 which is a switching circuit operating in response to transmitted energy from transmitter driver 62 to connect lines 52 to either transmit lines 58 or receive lines 60. Transmit lines 58 are connected to transducer energization signals from transmit drivers 62. Transmit drivers 62 are controlled by transmit timing circuit 64 and by transmit level control circuit 66. Circuit 64 controls the timing for the energization of various channels and, where appropriate, segments and the duration of transmit drive signals. Transmit timing 64 also has a frequency selection input on line 68 from control processor 50 which controls the ultrasonic frequency of the drive signals to the transducers. Additional inputs to transmit timing circuit 64 are line or aperture number lines 48 and steering angle lines 70. Steering angle line 70 from control processor 50 indicate the steering angle or angles at which scan lines are currently being transmitted. Drive level control 66 controls the power or gain of the transmit signals from drivers 62. Lines 48 are also connected as an input to drive level control 66.

Lines 60 are connected through time gain control (TGC) amplifier 72 to variable analog delay circuits 74. Both of these circuits receive inputs from timing lines 76 from control processor 50 and the line or aperture number lines 48. Steering angle lines 70 are a final input to delay 74. As is well-known in the art, since the received signals are weakened with increasing depth, TGC amplifiers are provided which increase gain as a function of depth to maintain a substantially uniform output. Variable analog delays 74 are standard devices utilized for controlling receive focus in an ultrasonic scanning system.

The outputs from delays 74 are summed in summing circuit 78 and the resulting output is passed through conventional bandpass filter circuit 80 and envelope detectors 82 to A/D converters 84. A/D converters 84 also have an input from line number lines 48 and timing lines 76. The outputs from converters 84 are applied to line buffer memory or memories 86. It is in the buffer memories that line splicing is performed, only the portion of the received signal for a given steering angle at the depth for which the line or aperture is focused being stored in the buffer memory. The line or aperture number on line 48 is applied as an additional input to memory 86 to facilitate this process. Once the scan lines for a given steering angle have been assembled in memory 86, this information is passed on to appropriate circuitry including frame buffers in a standard display system 88.

Figure 7B:
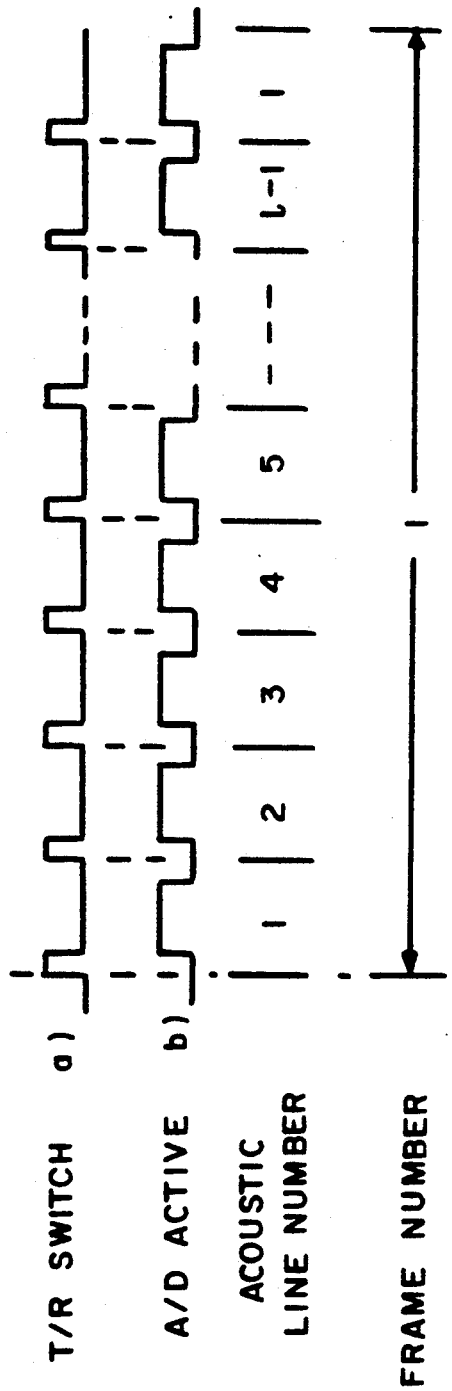

FIGS. 7A and 7B illustrate the general timing for operation of the system shown in FIG. 6. The diagrams of FIGS. 7A and 7B are for a standard system without the enhancements introduced in accordance with the teachings of this invention and are used for comparison purposes in understanding the changes in the basic system required to implement the various features of this invention.

Referring first to FIG. 7A, the timing for the transmission and receipt of a single scan line is shown. Referring to this figure, it is seen that transmit received (T/R) switch 54 is initially in a transmit mode, and remains in this mode for a relatively short period. During most of the scan line cycle, switch 54 is in its "RECEIVE" mode. Line (b) shows that transmit driver 62 is energized during the latter portion of the transmit mode and that switch 54 is switched to receive mode when the transmit drive pulse terminates. Line (c) indicates that TGC amplifier 72 is in a low gain state until echo signals start to be received. As echo signals are received from progressively greater depths, the TGC gain increases in a predetermined way, with maximum gain occurring at the end of the receive mode. Line (d) indicates that the variable analog delays 74 are geometry specific for the particular array as well as the steering angle and desired focusing depth for the scan line. Finally, line (e) indicates that A/D converter 84 is turned on at the beginning of the receive mode and remains on until signals from a predetermined depth have been received. A/D converter 84 may thus be utilized to control the range for the scan line. FIG. 7B illustrates the timing for a single display frame, lines (a) and (b) of FIG. 7B corresponding to lines (b) and (e), respectively, of FIG. 7A.

Figure 8:
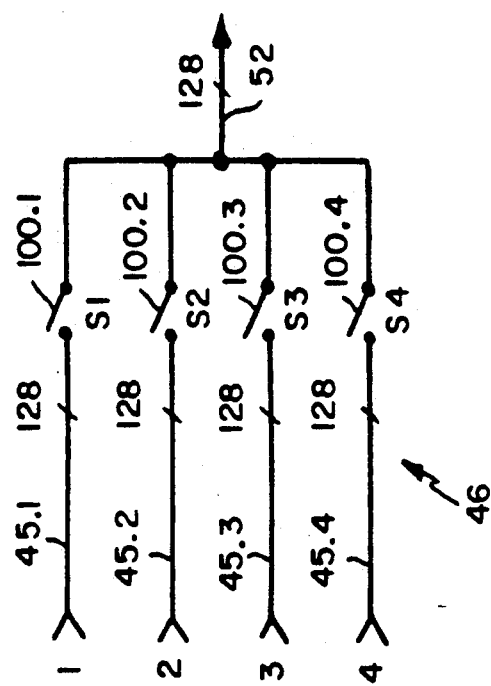
FIG. 8 is a simplified schematic diagram of a combining network suitable for use as the combining network in FIG. 4.

Referring to FIG. 8, a simplified diagram for a combining circuit 46 is shown. In this diagram, each of the cables 45 is shown connected to a corresponding switch array 100.1-100.4. The other side of each of the switches 100 are connected together to output lines 52. While the circuit 46 in FIG. 8 only switches the segments in the elevation direction, or in other words provide multiple apertures in the elevation direction, additional conventional switching may be provided for the 128 lines interfacing with each switch 100 to provide for multiple apertures in the azimuth direction. More specifically, each of the switches 100 may be formed of multiple switches which are selectively enabled for providing azimuth apertures. Switches 100 would typically be electronic switches of the type previously suggested. Further, while combining circuits 46 may be at the signal processor end of cables 45, it is also possible for lines 52 to be the transducer head cable, with combining circuits 46 being at the transducer-array end of the cable. This is an alternative to the technique shown in FIG. 5 for reducing the number of lines in the cable.

Figure 9:
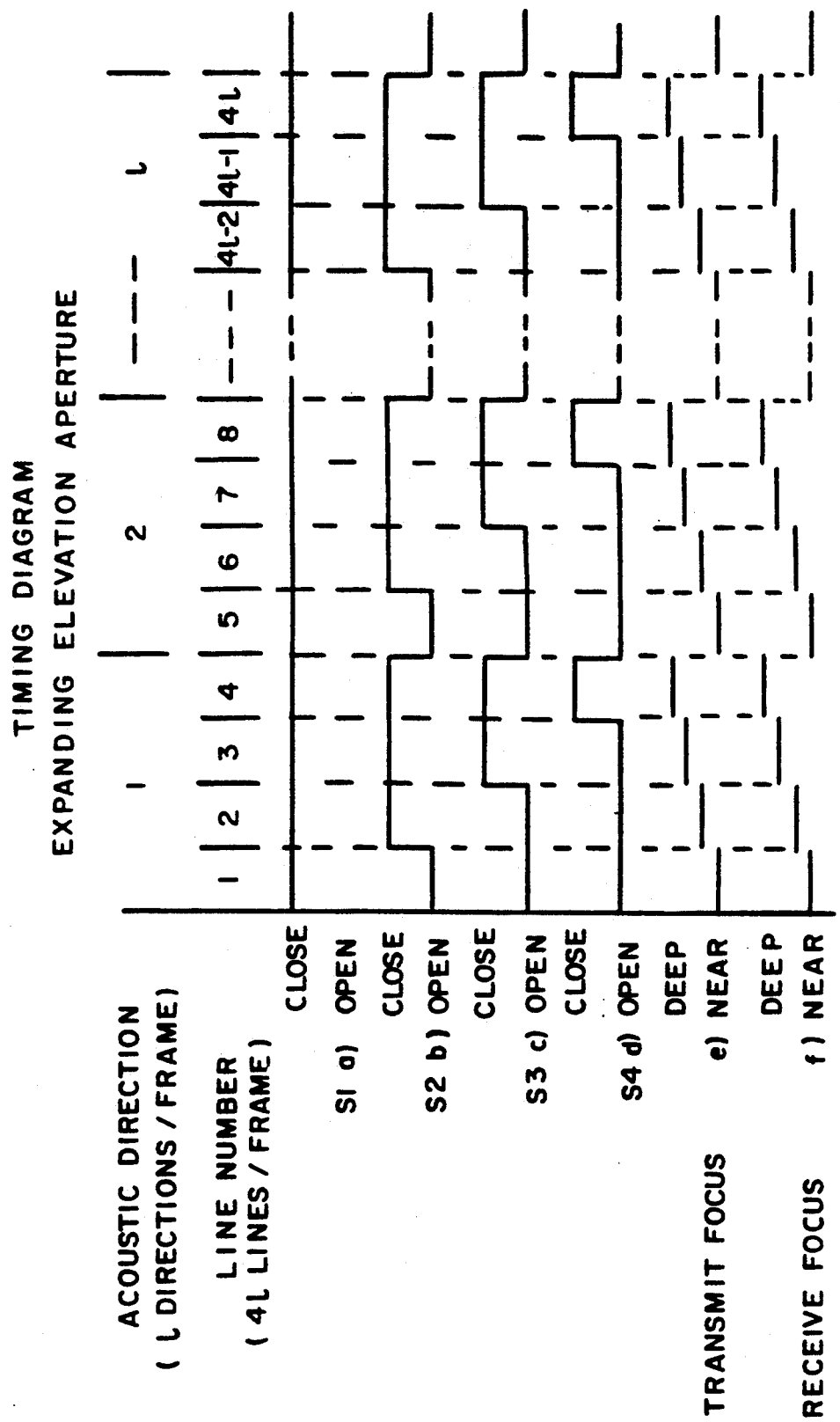
FIG. 9 is a timing diagram for one embodiment of the invention having an expanding elevation aperture.

FIG. 9 illustrates a preferred way in which the switches 100.1-100.4 may be utilized to control the transmit aperture. In FIG. 9, an expanding aperture is provided. Therefore, line (a) indicates that switch 100.1 is on or closed during the transmission and receipt of all four scan lines transmitted at each given steering angle. Switch 100.2, which corresponds to the second smallest aperture, aperture 32 (FIG. 3A) is closed only during the transmission and receipt of the second, third and fourth scan lines (line (b)). Similarly, as shown on lines (c) and (d), switch 100.3 is closed for only the third and fourth scan lines and switch 100.4, corresponding to outside aperture 34 (FIGS. 3A) is closed only during scan line 4. The aperture thus expands, adding additional transducer array elements (channels) and segments for each aperture. As illustrated on lines (e) and (f) of FIG. 9, with each expansion of the aperture, the focus both for transmit and receive moves deeper into the body or other object being scanned. A less desirable alternative arrangement for controlling elevation aperture is to use only a single aperture for each scan line rather than an expanding aperture.

Figure 10A:
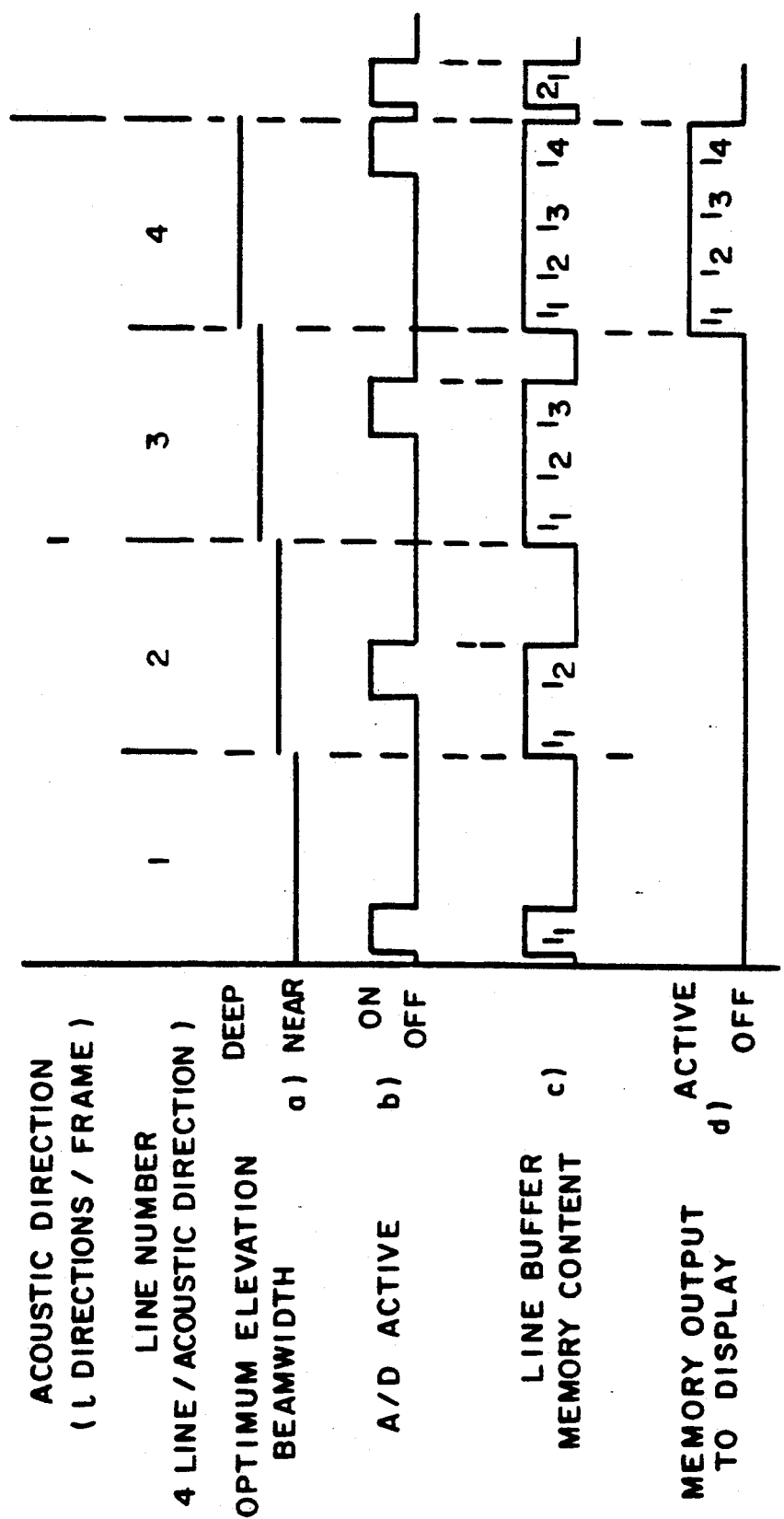
FIGS. 10A, 10B and 10C are diagrams illustrating line splicing with varying elevation aperture, azimuth bandwidth and frequency bandwidth, respectively.

FIG. 10A illustrates how line splicing is accomplished in line buffer memory 86 (FIG. 6). Basically, this is accomplished by turning on or activating A/D converter 84 only during the portion of each receive cycle when echo signals from the depth of interest for the particular scan line are being received. Buffer memory 86 also has an input from line 48 so that it knows where the information currently being received is to be stored in its buffer. Where the scan lines are transmitted sequentially, this may not be necessary since each received digital signal can merely be stored in the next succeeding memory position in the buffer. However, as will be discussed later, the scan lines at a given steering angle may not always be transmitted sequentially and it may, therefore, be necessary for there to be a line number input to the buffer 86 so that echoes received for a given scan line are stored in the proper position in the buffer.

FIG. 10A illustrates the above with line (a) showing the optimum elevation beam width for each succeeding scan line at a given steering angle. Line (b) illustrates the period during each scan line when A/D converter 84 is activated. It is seen that this period occurs later in the receive cycle for each succeeding scan line, with the periods that the A/D is on or activated for the combined four scan lines spanning the entire receive cycle. Thus, the time at which the A/D converter is turned off or deactivated for one scan line is substantially identical to the time the A/D is activated for the succeeding scan line so that there is substantially no overlap and no gaps in the depths for which information is stored in buffer 86. Line (c) illustrates the accumulation of echo data in buffer 86 for the succeeding scan lines and line (d) illustrates the contents of this buffer which is transmitted to display system 88.

Figure 10B:
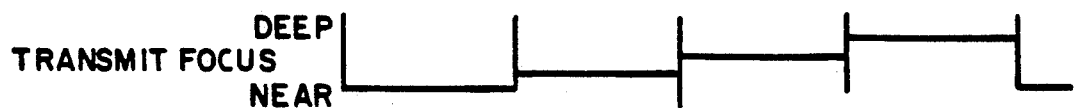

In the discussion above, the variable aperture was assumed to have occurred only in the elevation direction. However, enhanced resolution can be obtained by also controlling aperture in the azimuth direction as previously discussed. The number of apertures in the azimuth and elevation directions may differ; however, for optimum performance with the transmission of multiple scan lines, the number of apertures would typically be the same, with a different aperture being utilized for each scan line. If desired, the azimuth aperture may be made continuously variable during the receive portion of each scan line while the elevation aperture is only switched, thus further enhancing resolution. Techniques for continuously varying the receive aperture in the azimuth direction are known in the art, for example, varying the delays in receive delay line 74. It is desirable that if any switching occurs during a receive cycle, this be done quietly enough so as not to introduce switching artifacts into the image. Increasing the azimuth aperture is one way of controlling or improving beam width in the azimuth direction for successive scan lines as illustrated in FIG. 10B. Decreasing azimuth beam width to enhance resolution may also be accomplished by suitably controlling analog delay 74.

It is well-known in the ultrasonic scanning art that better resolution can be obtained by increasing the ultrasonic frequency. However, high frequency ultrasonic signals attenuate more quickly in the body being scanned. Therefore, where a single ultrasonic pulse is transmitted for a given steering angle, the frequency of such pulse or scan line must be sufficiently low to be able to reach the maximum depth of interest and have an echo signal return from such depth without undue attenuation. Thus, the ultrasonic transmit frequency utilized represents a compromise between the high frequency desired for optimum resolution and lower frequencies required to avoid excessive attenuation.

Figure 10C:
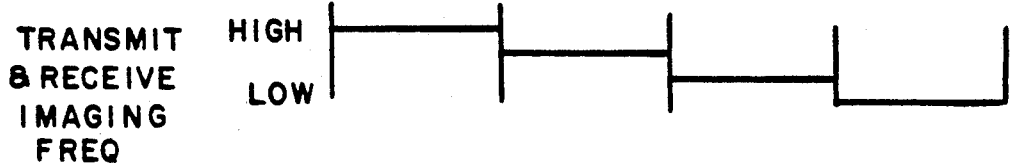

Since this invention employs multiple scan lines at a given steering angle, each of which is focused to a selected depth, the frequency for each of these scan lines can be selected to be the highest frequency which can be used for the given depth without undue attenuation. This permits higher frequency signals to be utilized for the small aperture scan focused at near or shallow depths with progressively lower frequencies being used for the succeeding scans focused at greater depths. FIG. 10C illustrates this with each succeeding scan line being at a progressively lower frequency.

One problem with the technique described above of shooting or transmitting multiple scan lines at a given steering angle is that it results in a significant degradation of system frame rate. In particular, where two lines are transmitted at each steering angle, the time required to complete a single scan is basically doubled, reducing the frame rate by 50%. Where four scan lines are transmitted at each steering angle, the frame rate becomes one-fourth of that for conventional systems. Such reduced frame rate increases the time required to do a scan or exam, but does not normally degrade the image where the object being viewed is stationary, such as in many industrial applications, and in medical applications where an organ such as the liver is being viewed. However, the reduced frame rate can cause a serious image problem where moving organs such as the heart are being viewed. Therefore, it is desirable that techniques be provided for enhancing the frame rate so as to mitigate this problem. The following is a discussion of various embodiments of the invention for effecting such an increase in frame rate.

Figure 11A:
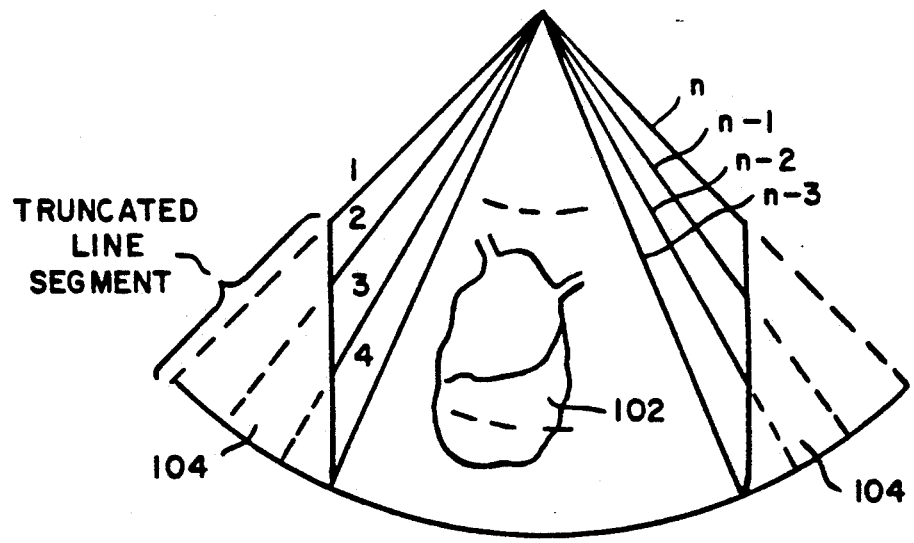
FIG. 11A is a diagram illustrating a single scan frame as such frame might be truncated to enhance frame rate.
Figure 11B:
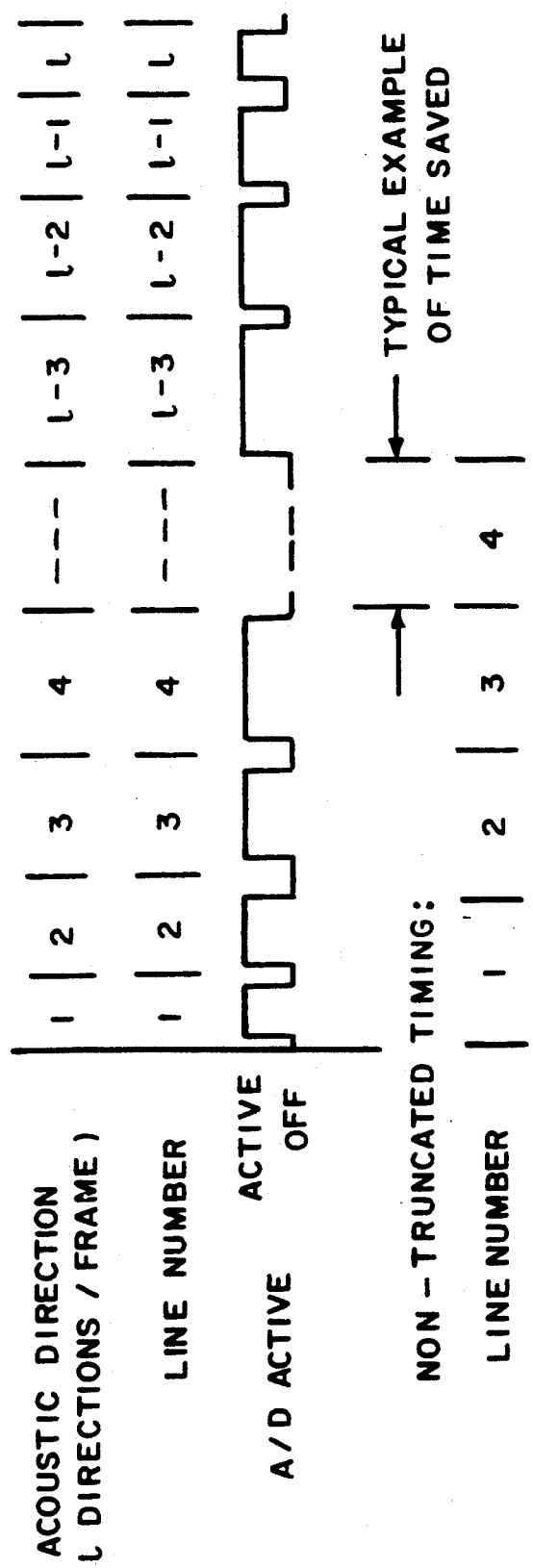
FIG. 11B is a timing diagram for a truncated sector display of the type shown in FIG. 11A.

FIGS. 11A and 11B illustrate one way in which frame rate may be enhanced, namely, by truncating the scan to eliminate areas not containing organs or other items of interest. For example, referring to FIG. 11A, if all that is of interest is the heart 102 and immediately surrounding environs, scans in the regions 104 could be eliminated without any loss of useful information. This is generally accomplished by making scan lines 3, 2 and 1 progressively shorter and by also making scan lines n−2, n−1 and n progressively shorter. It should be noted that there would, in fact, be many more scan lines involved in such a truncation operation, but only three lines are shown on each side for purposes of illustration.

FIG. 11B illustrates the activation period for each of the scan lines shown in FIG. 11A. Thus, it is seen that the scan line for steering angle No. 1 is active for the shortest period of time with scan lines at steering angles 2, 3 and 4 being active for progressively longer time periods. Similarly, scan lines at directions n−3, n−2, n 1 and n are active for progressively shorter durations. Scan lines between scan line 4 and n−3 would be on for the full duration, or in other words for the duration of scan lines 4 and n−3. The last line of FIG. 11B shows that by utilizing the truncation technique, it is possible to reduce some portion of the scanning time.

It should be noted that while only a single scan line is shown being transmitted at each of the steering angles for purposes of illustration in FIGS. 11A and 11B, a plurality of scan lines would actually be transmitted at each of these angles in accordance with the teachings of this invention. Each of this plurality of scan lines would be truncated as shown.

The truncation of the scan lines at the selected angles may be accomplished in a number of ways. For a preferred embodiment, it is accomplished by reducing the drive level from control 66 to the transmit drivers for these lines. A corresponding increase may be required in the receive level at TGC amplifier 72 in order to maintain a uniform signal-to-noise ratio. It may also be desirable to increase the transmit frequency by applying a suitable control to line 68 for the scan lines at the angles to be truncated since the increased frequency will enhance attenuation of these lines.

Figure 12A:
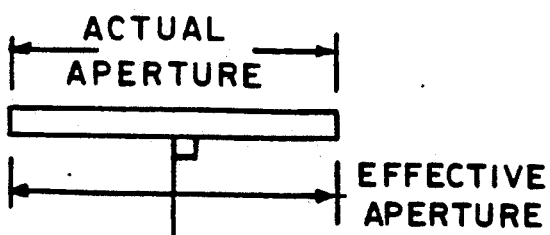
FIGS. 12A and 12B are diagrams illustrating effective aperture at different steering angles.
Figure 12B:
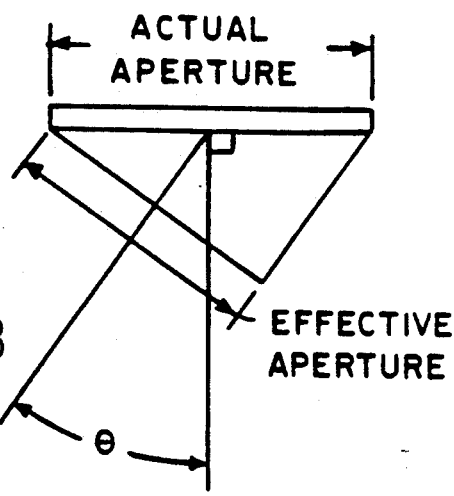
Figure 12C:
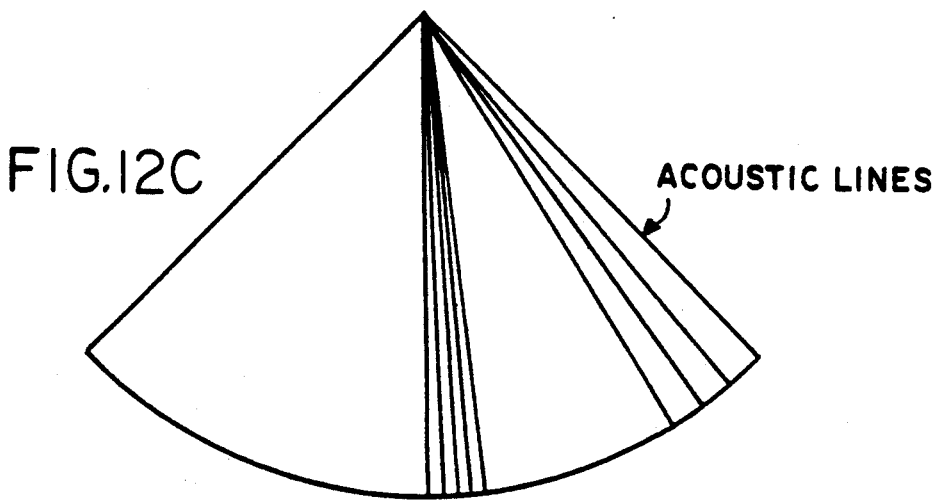
FIG. 12C is a diagram illustrating a scan pattern wherein line spacing varies as the cosine of the steering angle.

FIGS. 12A–C illustrate another technique which may be utilized to increase frame rate. It is known that the effective aperture for a given scan varies as a function of the cosine of the steering angle $\theta$. Thus: effective aperture = (actual aperture)(cos $\theta$) Beam width is known to be inversely proportional to effective aperture. Thus, beam width is a minimum near the center of the scan where $\theta = 0°$ and increases toward the wings as the angle $\theta$ increases. This is illustrated by FIGS. 12A and 12B.

Since a lesser number of scan lines are required where the beam width is wider, the total number of steering angles at which beams are transmitted could be reduced, without having areas which are not covered by a scan, by having the spacing between successive steering angles vary as a function of cos $\theta$, and programming transmit timing circuit 64 and receive analog delay circuit 74 in response to the steering angle input on line 70. FIG. 12C illustrates a scan where the steering angle spacing is varied in this manner.

Figure 13:
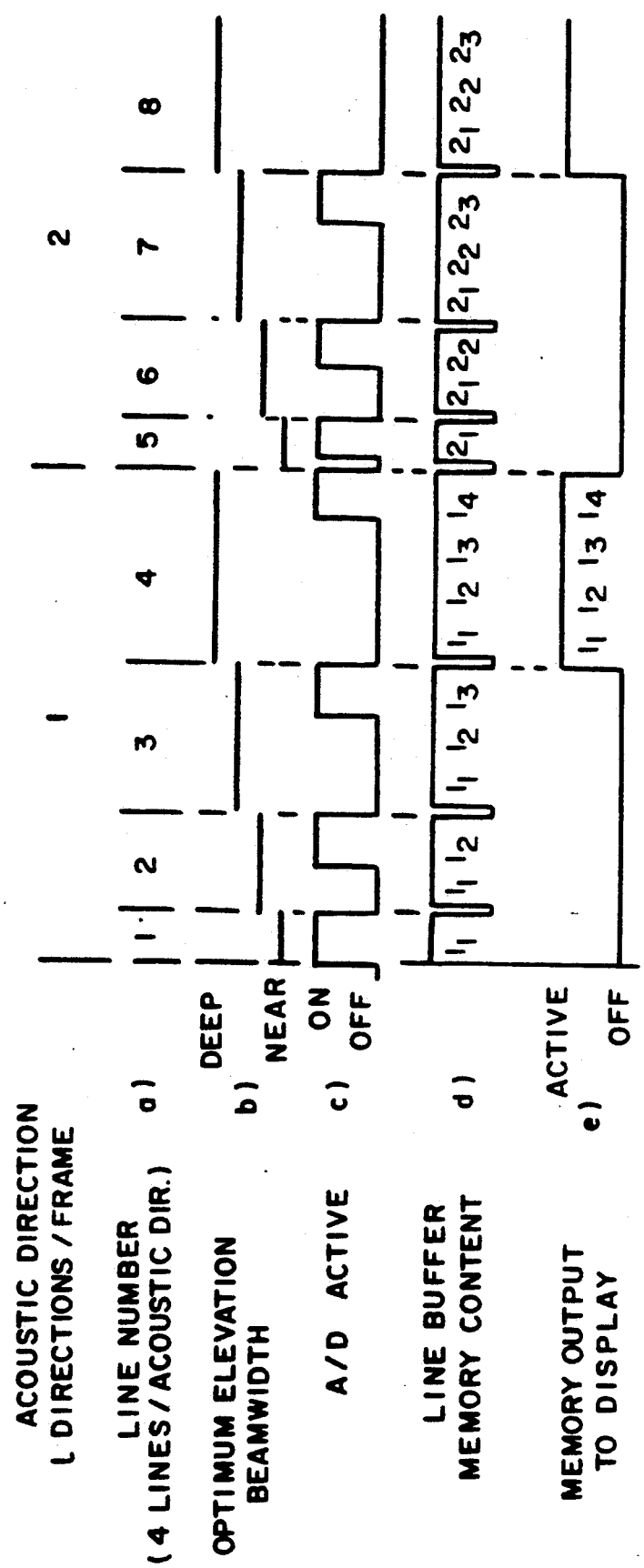
FIG. 13 is a timing diagram illustrating variable line duration for the different scan lines transmitted at a given steering angle.
Figure 14:
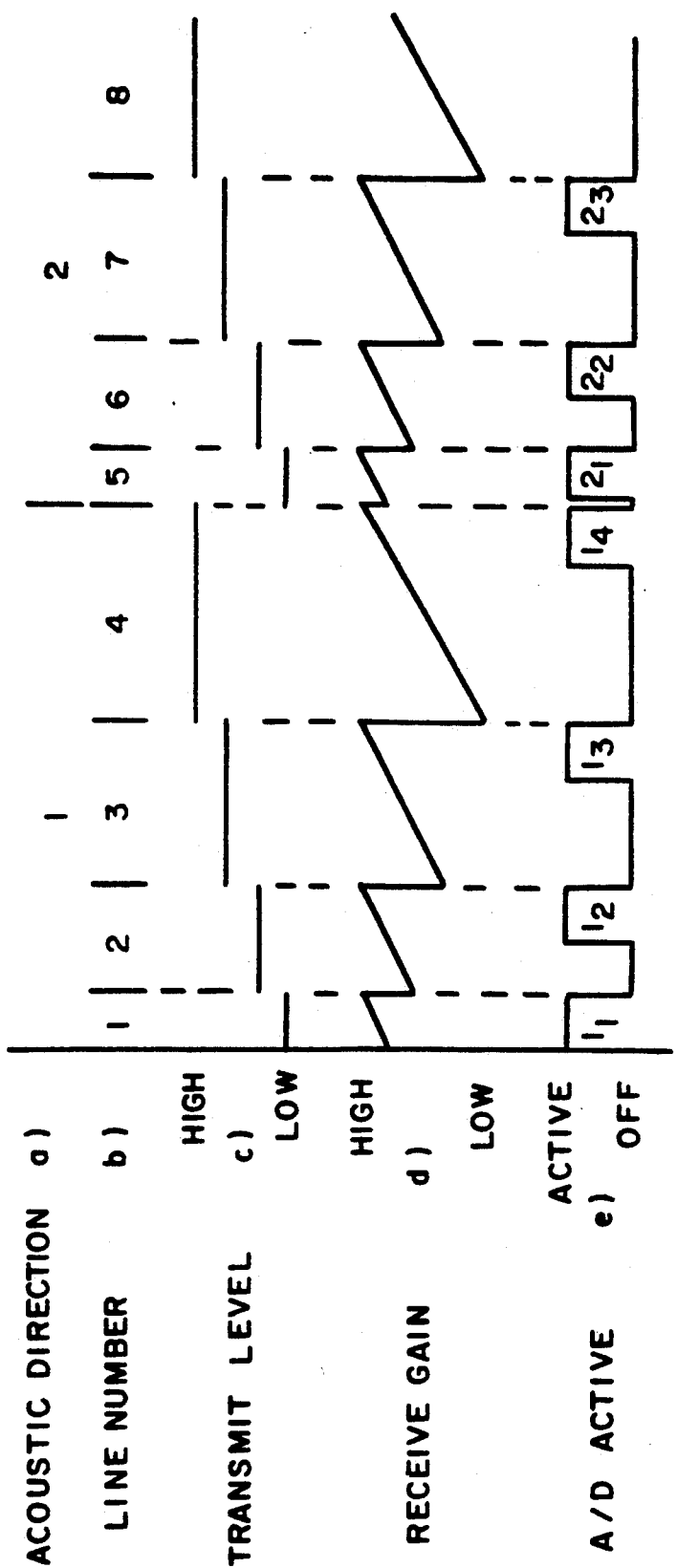
FIG. 14 is a diagram illustrating exemplary transmit and receive gain levels for the scan lines of FIG. 13.

FIGS. 13 and 14 illustrate another manner in which frame rate may be enhanced. For this embodiment of the invention, each scan line has a duration which is substantially equal to the time required for echo signals to be received by the transducer array from the depths for which the aperture for such scan line is focused and is to be utilized. Thus, as illustrated on lines (a) and (b), with four scan lines per steering angle, the duration of the scan lines increase as the depth of scan for the lines increases. From lines (c) and (d), it is seen that the A/D converter 84 is active to store in buffer 86 the information from scan 1 during substantially the entire scan, and the information from the remaining scan lines during the last portion of such scan line. Therefore, each scan line lasts only so long as is required to obtain the requisite echo signals.

FIG. 14 illustrates how this is accomplished. Referring to line (c) of FIG. 14, it is seen that the transmit level for the signals is low for line 1 and increases for the succeeding lines. As was previously discussed, it may be desirable that a higher frequency signal be used for line 1 with progressively lower frequency signals for the succeeding lines. This also results in the more rapid attenuation of the early signals as well as enhanced resolution. By proper selection of transmit signal and frequency, the signal can be reduced to the point where echoes are substantially fully attenuated beyond the depth of interest. As illustrated by line (e), the receive gain for TGC amplifier 72 is increased for line 1 and decreases progressively for the succeeding lines to compensate for the reduced transmit levels and higher frequency. Unwanted echoes from unused zones of the scan line are reduced by sharply dropping the receive gain at the end of the area of interest for each scan line and by not utilizing the first portion of the receive signal for subsequent scan lines where reverberation noise from the preceding scan is most likely to occur. This is illustrated by line (e) of FIG. 14 where it is seen that the A/D converter is active only during the last portion of each scan line. Using this technique, a scan with four scan lines per steering angle takes only 2½ times as long as a standard scan rather than four times as long and a scan with two apertures takes only 1½ times as long rather than twice as long.

Another way in which frame rate may be enhanced is to utilize the extra scan lines at a given steering angle only in areas of interest. Thus, if the area of interest in a particular scan were in a left region of the display, the extra scan lines at a given steering angle could be transmitted for only that region, while if the area of interest was deep in the body, scan lines at selected steering angles would be transmitted only for the deeper depths where resolution is otherwise normally degraded.

Figure 15A:
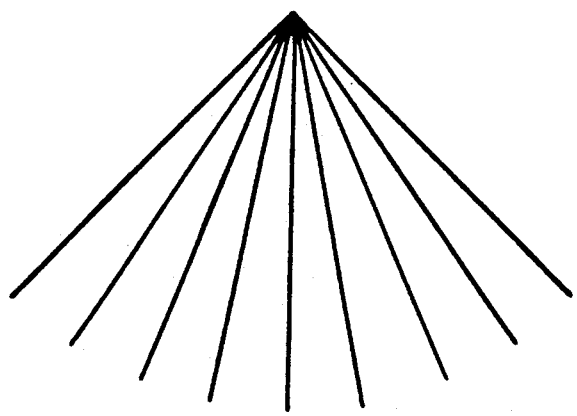
FIG. 15A illustrates a conventional sector scan with complete scan lines being transmitted and received a substantially evenly spaced steering angles.
Figure 15B:
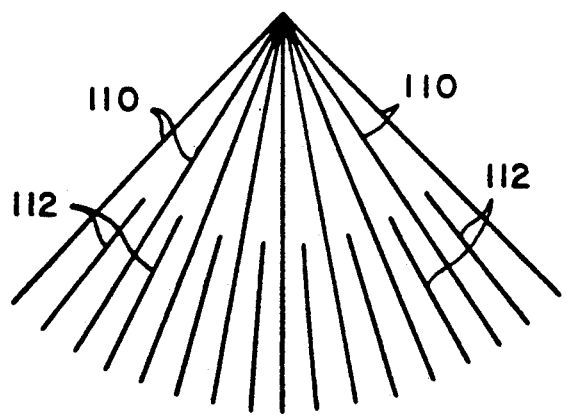
FIG. 15B illustrates an alternative sector scan pattern wherein extra scan lines are interspersed at deep ranges.

Thus, referring to FIG. 15A, a conventional scan is shown wherein scan lines are transmitted at a plurality of substantially uniformly spaced steering angles. FIG. 15B illustrates the situation where the area of particular interest is at the greater depths, with there being two scan lines per steering angle. For the lines transmitted at steering angles 110, both scan lines are transmitted while for the intermediate steering angles 112, only the outer aperture scan line is transmitted. Assuming that beam width does not substantially increase with depth because of the enhanced focusing at such depth provided in accordance with the teachings of this invention to increase spatial sampling, the generating of scan lines in the manner shown in FIG. 15B may be required, or at least be desirable in some situations, since the beam width may not be sufficient to cover the entire area at deeper depths.

One potential problem with transmitting lines of different length at the same steering angle is that leftover reverberation signals from an immediately preceding short duration line could superimpose as an echo on a succeeding longer line. This is less of a problem when a short line follows a long line since the long line becomes sufficiently attenuated at its outer extremities to prevent such reverberations.

As was discussed in conjunction with FIGS. 13 and 14, this problem can be reduced by using a lower transmit power for the small aperture shorter lines and by increasing the receive gain for the short lines to maintain an adequate signal-to-noise level. Ideally, the transmit and receive gains would be adjusted for each of the lines so as to maintain a substantially constant electronic signal-to-noise level at the receiver for all lines. Further, as was mentioned previously, this problem is further reduced by the fact that the first portion of the signal received for each long line, the portion of the signal where reverberations are most likely to occur, is not utilized. Alternatively, the problem of spurious reverberations might be reduced by reversing the order in which the lines are transmitted, with the long lines for the deeper depth being shot first, followed by successively shorter lines for the shallower depths.

Where reverberations are a problem and problems of temporal discordance or discontinuties in the image can be resolved, it may be possible to overcome the problem by varying the direction in which long and short lines are being shot. More particularly, a short line from a small aperture may be transmitted at a given steering angle with the next line being transmitted being a long line at a different steering angle. The second steering angle is chosen to minimize interference from the acoustic data of the preceding short line. More particularly, it is desirable that the long line after a short line be transmitted at an angle which is at least 15° spaced, and preferably 30° spaced from the steering angle at which the short line was transmitted. This assures that there will be no reverberation noise from the short line in the long line. Since, for reasons discussed above, there is little or no interference or reverberation in a short line from a preceding long line, the line following a long line may be a short line transmitted in the same direction as the preceding long line. Another similar way in which frame rate may be enhanced is by simultaneously transmitting two scan lines at different spaced steering angles.

While a number of different embodiments have been discussed above for enhancing frame rate, it is apparent that two or more such techniques could be employed simultaneously for frame rate enhancement. Thus, the use of short lines for small apertures and longer lines for larger apertures could be combined with the truncating of the scan area (FIGS. 11A and 11B) to achieve even greater frame rate enhancement. Further, all of the techniques described above, whether described in conjunction with a two-aperture or a four-aperture transducer, could be utilized with a transducer array having any desired number of apertures and the number of apertures actually utilized will depend on the degree of resolution enhancement required and the degree of frame rate degradation which can be tolerated in order to obtain such resolution enhancement.

Further, it should be understood that while the various techniques described above for achieving resolution enhancement and frame rate enhancement have been described with reference to a system having a control computer and various special purpose function blocks, each of which may itself contain a microprocessor or special purpose processing circuitry, most of the switching and control functions could be performed by a suitably programmed general purpose computer or special purpose circuitry could be provided for performing all of the functions. A mix of special purpose and general purpose circuitry along the lines generally discussed above is considered preferable.

Thus, while the invention has been particularly shown and described above with reference to various preferred embodiments, the foregoing and other changes in form and detail may be made therein by one skilled in the art without departing from the spirit and scope of the invention.

What is claimed is:

1. An ultrasonic transducer system comprising
an ultrasonic transducer array having M transducer channels in the azimuth direction, with at least selected ones of said transducer channels being divided into N segments in the elevation direction, said segments being grouped to form E elevation apertures M, N and E each being an integer of two or more;
means for providing a selected focal length for each of said elevation apertures at a selected depth, the focal length increasing with the size of the elevation apertures;
means for energizing selected transducer channel segments to transmit scan lines at selected steering angles, said energizing means including means operative for at least selected ones of the steering angles for energizing at different times the segments for at least two different elevation apertures, whereby at least two scan lines are transmitted at each such steering angle, echo signals being received from the transducer array in response to each energization of the transducers; and means for line splicing the received echo signals for said at least selected steering angles so as to use from each received scan line the portion thereof for which the corresponding elevation aperture is focused.

2. A system as claimed in claim 1 including means for controlling the transducer array aperture in the elevation direction which is utilized for receiving each scan line, the receive elevation aperture for a scan line being related to the transmit elevation aperture in a predetermined way to achieve a selected response.

3. A system as claimed in claim 2 wherein the transmit and receive elevation apertures for a given scan line are the same.

4. A system as claimed in claim 1 wherein said means for providing a selected focal length includes a segmented lens having a different segment configuration over each elevation aperture to provide the selected focal length.

5. A system as claimed in claim 1 wherein said means for providing a selected focal length includes a segmented transducer surface having a different segment configuration for each elevation aperture to provide the selected focal length.

6. A system as claimed in claim 1 wherein said channels are grouped to form a plurality of apertures in the azimuth direction, and including means for establishing an azimuth focus for each of said azimuth apertures.

7. A system as claimed in claim 6 wherein there are E azimuth apertures, and wherein the azimuth focus for each azimuth aperture is the same as the elevation focus for the corresponding elevation aperture, said means for energizing energizing the transducer channels and segments for at least two different apertures at different times for the at least selected ones of the steering angles.

8. A system as claimed in claim 1 wherein the segments of each elevation aperture are included in each larger elevation aperture.

9. A system as claimed in claim 1 wherein the steering angles for which scan lines are transmitted for at least two different elevation apertures are all steering angles at which scan lines are transmitted.

10. A system as claimed in claim 1 including means for enhancing the resolution of the system.

11. A system as claimed in claim 10 wherein said resolution enhancement means includes means for providing a different azimuth beam width for each elevation aperture, the azimuth beam width being matched to the focal length for the aperture.

12. A system as claimed in claim 10 wherein said resolution enhancement means includes means for providing a different transmit frequency for each elevation aperture, the transmit frequency being matched to the focal length for the aperture.

13. A system as claimed in claim 1 wherein said means for line splicing includes at least one line buffer, and means for storing in said buffer the portion of each scan line for a given steering angle which is for the focal length at which the corresponding elevation aperture is focused.

14. A system as claimed in claim 1 wherein said means for energizing causes a scan line for each E elevation aperture to be transmitted for a plurality of substantially uniformly spaced steering angles, and causes scan lines for a selected number of elevation apertures less than E to be transmitted for steering angles intermediate to said plurality of steering angles.

15. A system as claimed in claim 14 wherein the selected number of elevation apertures for the intermediate steering angles are one or more elevation apertures having the deepest focal length.

16. A system as claimed in claim 1 wherein the system has a frame rate based on the time required to complete a scan through a selected range of steering angles, and including means for enhancing the system frame rate.

17. A system as claimed in claim 16 wherein said means for enhancing includes means for reducing the scan depth for selected ones of said scan lines.

18. A system as claimed in claim 17 wherein steering angles for a scan extend from $-D°$ to $+D°$ and wherein the scan depth of the scan lines are reduced for steering angles at the $-D°$ and $+D°$ ends of the scan, the reduction in scan depth increasing as the steering angles approach $-D°$ and $+D°$ ends.

19. A system as claimed in claim 17 wherein the selected ones of said scan lines are the scan lines for the elevation apertures having the shortest focal length, the scan depth for such scan lines corresponding to the greatest depth for which received echo signals for such scan lines are utilized by said means for line splicing.

20. A system as claimed in claim 17 wherein said means for reducing scan depth includes means for reducing power-provided by said means for energizing for transmitting the scan line.

21. A system as claimed in claim 17 wherein said means for reducing scan depth includes means for increasing the frequency of the scan line having its depth reduced.

22. A system as claimed in claim 16 wherein the steering angles in the azimuth direction for a scan range from $-D°$ to $+D°$, and wherein the means for enhancing includes means for reducing the number of selected steering angles within said range at which said means for energizing causes scan lines to be transmitted.

23. A system as claimed in claim 22 wherein the spacing between adjacent selected steering angles varies inversely with $\cos \theta$, where $\theta$ is the steering angle.

24. A system as claimed in claim 1 including switch means operative in response to a change in the aperture being utilized for causing transducer channel segments for the appropriate aperture to be energized.

* * * * *